United States Patent [19]
Walton et al.

[11] Patent Number: 5,157,340
[45] Date of Patent: Oct. 20, 1992

[54] METHOD AND APPARATUS FOR DETECTING SOOT CONCENTRATION IN PARTICULATE TRAP

[75] Inventors: Frank B. Walton, Pinawa; Robert W. Kempster, Ottawa, both of Canada

[73] Assignee: Atomic Energy of Canada Limited, Pinawa, Canada

[21] Appl. No.: 562,752

[22] Filed: Aug. 6, 1990

[51] Int. Cl.⁵ .............................................. G01R 27/04
[52] U.S. Cl. ..................................... 324/641; 73/28.01
[58] Field of Search ............... 324/641, 639; 73/28.01, 73/28.04, 28.05

[56] References Cited

U.S. PATENT DOCUMENTS

| | | | |
|---|---|---|---|
| 3,104,354 | 9/1963 | Weinschel et al. | 324/641 |
| 3,277,366 | 10/1966 | Webb | 324/641 |
| 3,526,834 | 9/1970 | Brown | 324/641 |
| 4,042,879 | 8/1977 | Ho et al. | |
| 4,077,003 | 2/1978 | Rau | 324/338 |
| 4,135,131 | 1/1979 | Larsen et al. | 324/639 |
| 4,477,771 | 10/1984 | Nagy et al. | 324/636 |
| 4,507,602 | 3/1985 | Aguirre | |
| 4,580,441 | 4/1986 | Sakurai et al. | |
| 4,764,718 | 8/1988 | Revus et al. | 324/641 |
| 4,943,778 | 7/1990 | Osaki | 324/641 |
| 4,947,129 | 8/1990 | Helms et al. | 324/641 |

*Primary Examiner*—Jack B. Harvey
*Assistant Examiner*—Maura K. Regan
*Attorney, Agent, or Firm*—Davis, Bujold & Streck

[57] ABSTRACT

A method of detecting the accumulation of particulate material collected on a filter medium formed of dielectric material in a chamber having the property of a microwave waveguide or transmission line comprises the steps of exciting the chamber with a microwave signal and monitoring the transmission loss of the signal through the line to sense the effective dielectric loss factor and thereby to provide an indication of the concentration or level of particulate material accumulated on the filter medium.

10 Claims, 2 Drawing Sheets

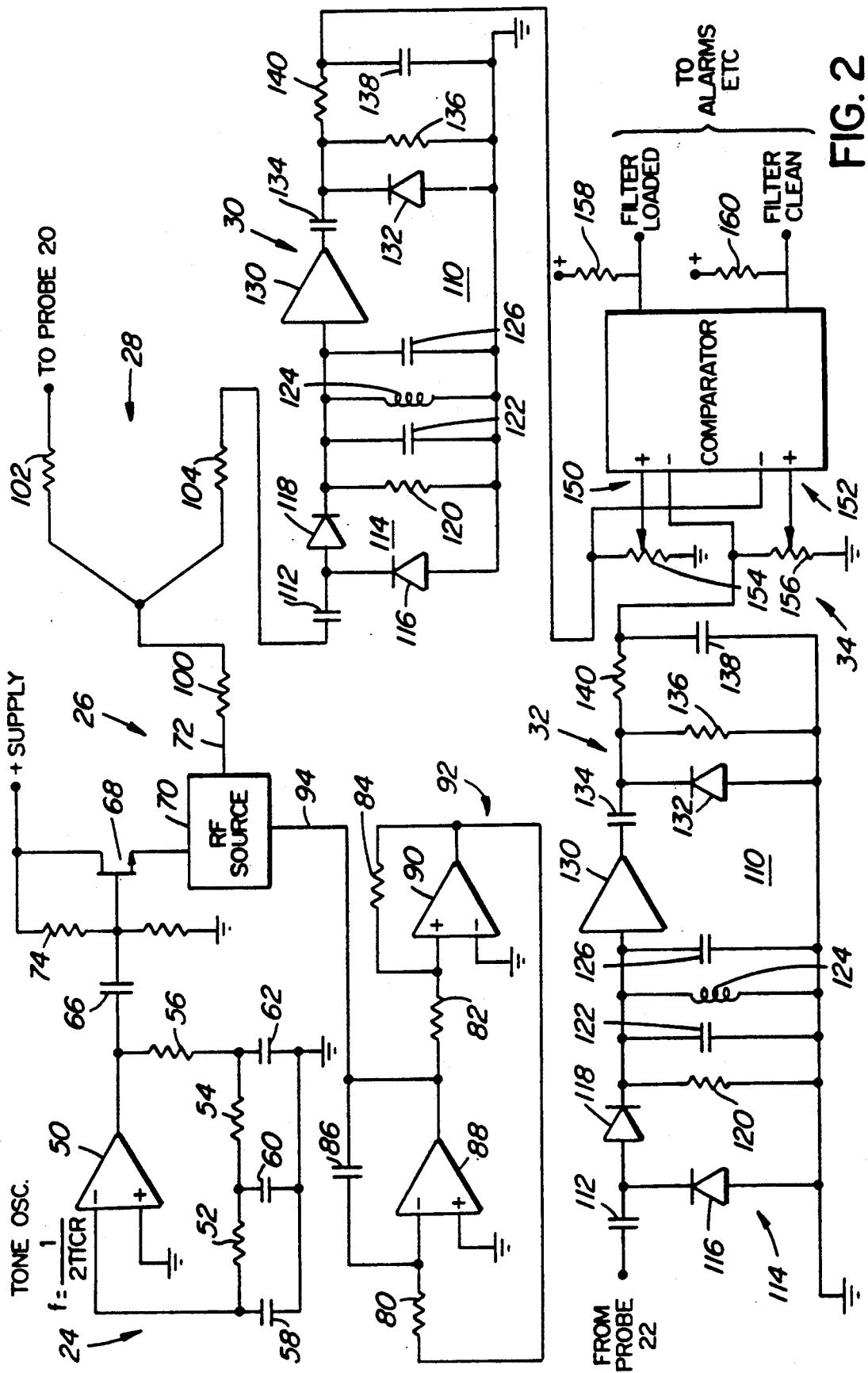

METHOD AND APPARATUS FOR DETECTING SOOT CONCENTRATION IN PARTICULATE TRAP

The present invention relates, in general, to a method and an apparatus for detecting the concentration or level of accumulation of microwave susceptible, particulate material on a filter medium and, more specifically, to a method and an apparatus for detecting soot accumulation on diesel engine exhaust filters.

BACKGROUND OF THE INVENTION

As is well known, a filter is placed in the exhaust system of diesel engines to remove soot from the exhaust gases of the engine. The filter must be changed or cleaned from time to time to ensure that soot accumulations do not adversely affect the operation of the engine. It is known to remove or incinerate the soot particles by subjecting the filter, in situ, to heat from a fuel burner or other heat generating device, or from suitable running of the engine. Incineration is to be performed when the accumulation has reached a level where further accumulation would adversely affect engine performance or that incineration would produce excessive temperatures and possibly damage the filter. There is a need, therefore, for a method and apparatus which monitors the level of soot accumulation and provides a signal when the accumulation reaches a predetermined level.

It is also known that soot accumulations exhibit dielectric properties. Accordingly, it is possible to monitor the level of soot accumulation on a diesel engine filter medium by detecting changes in the effective dielectric properties of the filter medium. By way of background, the complex permittivity of a material is comprised of two components: a real component called the dielectric constant and an imaginary component called the dielectric loss factor. Changes in either of these components can be detected using microwave interrogation methods.

One method of detecting changes in the effective dielectric constant involves exciting a microwave waveguide or transmission line, in which the filter is housed, with microwave energy at a fixed frequency and measuring the reflected power. For any RF system, a frequency can usually be found such that the electrical load, i.e. the filter medium, the diesel soot and the filter containment in this case, represents a matched impedance with respect to the power source. In other words, the equivalent electrical resistance, capacitance and/or inductance of the load are matched to the RF power source. When the load impedance is perfectly matched to the power source, all emitted RF power is absorbed by the load. If the impedance is not matched to the RF source, some of the RF power will be reflected from the load. The degree of load mismatch determines the amount of reflected power and hence reflected power can be used to measure the change in the effective dielectric constant.

U.S. Pat. No. 4,477,771 granted to the General Motors Corporation on Oct. 16, 1984 describes a method of detecting soot content in a particulate trap using this method. More specifically, the method is based on the principle of detecting changes in the effective dielectric constant only. The patent provides a filter housing which forms a closed, microwave resonance cavity in which a ceramic filter is placed. A single probe is positioned at one end of the cavity and behaves as both a transmitting and receiving antenna. A reflective screen is positioned at the opposite end of the cavity. All connecting exhaust pipe diameters are below the cutoff diameter of a circular waveguide needed to transmit the RF energy at the frequencies used in the device. The probe is connected to a microwave source through a directional coupler and an isolator. A detector is also connected to the probe through the directional coupler. In one mode of operation of the device, the microwave source is operated at the resonant frequency of the cavity when the filter is loaded with particulates to its maximum desired accumulation and the detector is operated to detect a null condition in the reflected signal which occurs at the resonant condition. Upon detecting such a condition, the detector generates an output signal operable to effect operation of a lamp or alarm. In a second embodiment, the reflective screen is eliminated and a second probe is positioned at the remote end of the cavity. One probe is connected to the power source and the other probe is connected to the detector.

It has been found that there are a number of technical and practical problems with this approach. First, the isolators and directional couplers are relatively complex devices needed to protect the RF source from the reflected power. From a practical point of view, the cost of these items would almost certainly preclude the device from being commercialized. Second, a power source of sufficient stability to allow long-term measurements at a single frequency without frequency drift would be prohibitively expensive. Third, and perhaps most importantly, the device tends to display poor sensitivity and is prone to large measurement errors due to the effect of temperature on the effective dielectric constant.

Another method involves exciting a microwave waveguide or transmission line with microwave energy at variable frequencies and measuring the reflected power. This is simply an extension of the method described in the General Motors patent. In accordance with this approach, the frequency is varied in order to minimize the reflected power. In effect, the frequency is varied in order to match the RF power source characteristics to the load impedance characteristics. Structurally, the device is the same as that described above except a variable frequency source is required. Frequency is used as the measurement parameter instead of reflected power. In addition the drawbacks discussed earlier, a variable frequency source and the required control logic would make this type of device prohibitively expensive.

SUMMARY OF THE INVENTION

The present invention seeks to provide a method and an apparatus which overcome the above described disadvantages by detecting changes in the effective dielectric loss factor as opposed to changes in the effective dielectric constant. In practice, this is achieved by exciting the filter chamber with microwave energy and measuring the transmission attenuation or loss due to changes in the filter effective dielectric loss factor caused by soot loading.

Thus, in accordance with one aspect of the present invention, there is provided a method of detecting the accumulation of particulate material collected on a filter medium formed of dielectric material and disposed in a chamber having the property of a microwave resonance waveguide or transmission line, the method comprising the steps of exciting the waveguide or transmission line with a microwave signal; and monitoring the transmission loss of the signal through the waveguide or transmission line to sense the effective dielectric loss factor thereof to provide an indication of the content of particulate material accumulated on the filter medium.

In accordance with one aspect of the present invention, there is provided an apparatus for detecting the accumulation of particulate material collected on a filter medium formed of dielectric material in a chamber having the property of a microwave waveguide transmission chamber, the apparatus comprising means for exciting the chamber with a microwave signal; and means for monitoring the transmission loss of the signal through the chamber to sense the effective dielectric loss factor thereof whereby to provide an indication of the content of particulate material accumulated on the filter medium.

BRIEF DESCRIPTION OF THE DRAWINGS

These and other features of the invention will become more apparent from the following description in which reference is made to the appended drawings wherein:

FIG. 2 is a schematic of an electrical circuit in accordance with an embodiment of the present invention;

DESCRIPTION OF PREFERRED EMBODIMENT

Figure 1:
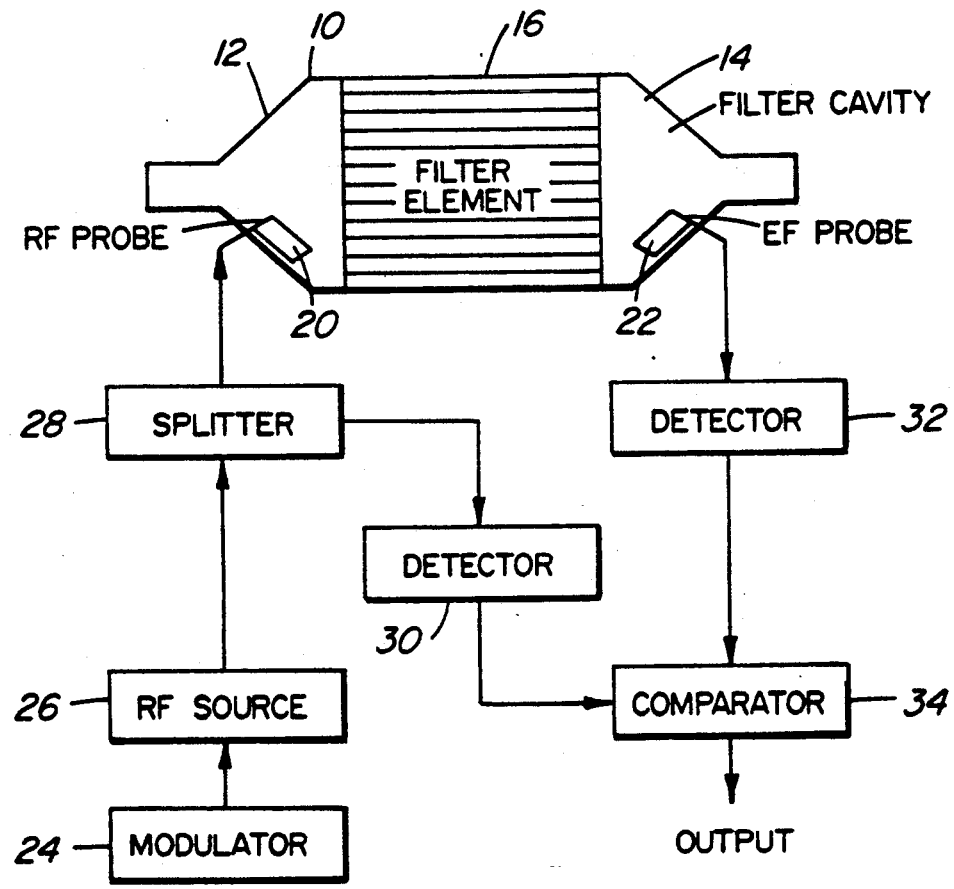
FIG. 1 is a diagrammatic, cross-sectional view of a diesel exhaust particulate trap or filter adapted for microwave detection of the soot accumulation and a block diagram of an electrical circuit for carrying out the method of the present invention.

FIG. 1 illustrates a steel, cylindrical filter housing 10 having a having frusto-conical steel end sections 12 and 14 adapted to the connected to engine exhaust pipes in a manner well known in the art. The housing is formed in such a manner that it behaves as a waveguide or microwave transmission line and includes a chamber 15 to receive a ceramic filter element 16 of suitable construction.

The construction of the filter and the housing do not form part of the present invention and, accordingly, neither component is described in detail herein. Suffice it to say that a large portion of the particulates which are carried into the housing by the exhaust gases are trapped and collected on the interior and exterior surfaces of the filter element. The collected particles build up to until, if left unattended, they eventually interfere with the performance of the engine. The soot particles affect both the dielectric constant and the dielectric loss factor properties of the filter. In practice, methods of detecting changes in the effective dielectric constant require measurement of parameters such as the power of the transmitted signal and the frequency of the signal as mentioned earlier which require expensive and precise equipment. Furthermore, the dielectric constant varies with temperature and, therefore, successful use of this method requires still further complexity. These difficulties can be overcome by the present invention as described below.

In accordance with the present invention, there is provided a method and an apparatus for detecting changes in the effective dielectric loss factor of the material in the chamber caused by changes in soot loading. In the preferred embodiment of the invention, this is achieved by detecting signal attenuation or loss of a microwave signal applied to the cavity. To that end, there is provided a first probe 20 which behaves as a transmitting antenna for RF power and a second probe 22 which serves as a receiving antenna. A modulator 24 generates an amplitude modulated tone signal which is fed to an RF source 26 which generates a carrier signal for the tone signal and applies the resulting signal to a splitter 28. Splitter 28 applies the signal to both transmitting probe 20 and a first detector 30. Detector 30 produces a reference output signal which is representative of the power of the signal prior to transmission. The use of an amplitude modulated signal allows the signal to be much more easily detected than by the method used in the aforementioned General Motors Corporation patent.

A second detector 32, electrically connected to second probe 22, produces an output signal representative of the power of the signal received by the second probe 22. The first and second detector output signals are applied to a comparator 34 which produces an output signal which is proportional to the difference in the signal strength of the transmitted and received signals. Accordingly, the comparator output signal is representative of the transmission loss through the filter medium which, in turn, is representative of the change in the effective dielectric loss factor caused by accumulation of soot on the filter. It will be seen therefore that when there is little or no accumulation in the filter, there will be only a small transmission loss in the signal strength. As the soot accumulation increases, the difference in signal strength between the transmitted and received signals changes, resulting eventually in an output signal from the comparator. The comparator can be designed to drive a variable output display or an indication when a predetermined level is reached, or both.

The power source is arranged to emit RF energy over a range of frequencies with the preferred frequency band being up to one octave, i.e. a 2 to 1 range, in frequency. An appropriate frequency band is 500 MHz to 1,000 MHz. There are three reasons for this. First, the average transmission loss through the filter over the selected frequency range results in better measurement sensitivity, i.e. attenuation per unit of soot present, and a more linear response as a function of RF signal attenuation than is possible at a single frequency. Second, it avoids problems associated with power source frequency drift with time. Third, the use of an averaging process demonstrably reduces the effects of temperature on transmission losses, i.e. the effects of temperature on soot and filter permittivity, which would otherwise require temperature compensation in single or narrow band frequency methods. The minimum frequency in the operating range is chosen to be above the cutoff frequency of a circular waveguide with the same diameter as the filter chamber. Frequencies below the cutoff frequency are greatly attenuated by chamber geometry producing poor measurement sensitivity for the determination of filter soot load.

With reference to FIG. 2, modulator 24 will be seen to be comprised of an operational amplifier 50 which, with resistors 52, 54 and 56 and capacitors 58, 60 and 62, forms a phase shift audio oscillator which provides a tone modulated signal along line 64. This signal is fed via capacitor 66 to the gate of a FET modulator transistor 68 which directly modulates the power supply to a frequency swept RF source 70, thereby imposing an AM audio tone on the RF signal output along line 72. Resistors 74 and 76 form the gate bias network for transistor 68.

Resistors 80, 82 and 84, capacitor 86 and operational amplifiers 88 and 90 form a sawtooth waveform sweep generator 92 which feeds a swept output signal to the frequency control port 94 of the RF source so as to cause the RF oscillator output to vary by up to one octave in frequency. The sweep rate is set by resistor 80 and capacitor 86.

The output of the RF source is applied to splitter 28 which is simply comprised of a resistor 100 in series with parallel connected resistors 102 and 104. The output of resistor 102 is fed to the transmit antenna or probe 20 while the output of resistor 104 is fed to the input of reference detector 30. For equal power division, the resistances of the three resistors are equal. The values of the resistances may be varied so that match is preserved with the system impedance but with most of the power passed to the soot filter.

Reference detector 30 and the signal detector 32 may be of identical construction as indicated by subcircuits 110 in FIG. 2. Each circuit 110 includes a capacitor 112 which provides DC isolation from a low-resistance source for a voltage-doubler signal detector 114 comprised of diodes 116 and 118. Resistors 120 and Capacitor 122 provide a level enhancing time constant for the detected modulation tone. Inductor 124 and capacitor 126 form a parallel tuned circuit at the tone frequency which curtails the passband and improves the signal to noise ratio. Capacitor 128 prevents inductor 124 from shorting resistor 120. Operational amplifier 130 amplifies the signal tone by about 30 dB. Diode 132 rectifies the amplified tone signal to DC, with capacitor 134 and resistor 136 setting the time constant and capacitor 138 and resistor 140 serving as a ripple filter. Each of the two detectors feed a respective input to the comparator.

Comparator 34 is formed with two sections generally designated by reference numerals 150 and 152. The reference detector output is fed directly to the negative input of the second section 152 and indirectly to the positive input of the first section 150 through a potentiometer 154. Similarly, the signal detector output is fed directly to the negative input of the first section 150 and indirectly to the positive input of the second section 152 through a potentiometer 156. The potentiometers serve to set the input levels from the signal and reference detectors to the two sections of the comparator. More specifically, in one section, potentiometer 154 sets its input below the output signal of the signal detector. As the signal level declines with increasing soot, a point is reached where the negative input to this section drops below the positive input and the output of the section is then pulled up by resistor 158. In the other section, potentiometer 156 is set so that the positive input is above the reference detector output only when the soot filter is clean. This serves as an optional check on the burn-clean cycle. With the signal above the reference detector, resistor 160 pulls up this output. The outputs are connected to indicator circuits not shown.

It will be understood that various modifications and alterations may be made to the present invention without departing from the spirit of the appended claims.

The embodiments of the invention in which an exclusive property of privilege is claimed are defined as follows:

1. A method of detecting the accumulation of particulate material collected on a filter medium formed of dielectric material in a chamber having the property of a microwave transmission line, said method comprising the steps of:

exciting said chamber with a microwave signal; and
   monitoring the transmission loss of said signal through said chamber to sense the effective dielectric loss factor thereof to provide an indication of the content of particulate material accumulated on said filter medium.

2. A method of detecting the accumulation of particulate material collected on a filter medium formed of dielectric material in a chamber having the property of a microwave transmission chamber, said method comprising the steps of:

exciting said chamber with an amplitude modulated RF excitation signal within a predetermined microwave frequency band; and
   monitoring the transmission loss of said signal through said chamber to sense the effective dielectric loss factor thereof to provide an indication of the content of particulate material accumulated on said filter medium.

3. A method of detecting the accumulation of particulate material on a filter medium formed of dielectric material in a chamber having the property of microwave transmission line, said method comprising the steps of:

exciting said chamber with an amplitude modulated RF excitation signal in the microwave range of frequencies;
   detecting the signal strength of said signal prior to exciting said chamber to produce a signal representative of the initial strength of said excitation signal;
   detecting the signal strength of said signal subsequent to transmission thereof through said chamber to produce a signal representative of the final strength of said excitation signal; and
   comparing said initial strength signal and said final strength signal to produce a signal representative of the transmission loss of said signal through said chamber to detect changes in the effective dielectric loss factor thereof, said signal indicating the content of particulate materials accumulated on said filter medium.

4. A method as defined in claim 3, said step of exciting said chamber including the step of varying the frequency of said excitation signal within a predetermined frequency band.

5. A method as defined in claim 4, wherein said step of varying the frequency of said signal comprising varying the frequency within a frequency band of up to one octave.

6. An apparatus for detecting the accumulation of particulate material collected on a filter medium formed of dielectric material in a chamber having the property of a microwave transmission line, said apparatus comprising:

means for exciting said chamber with a microwave signal; and
   means for monitoring the transmission loss of said signal through said chamber to sense the effective dielectric loss factor thereof to provide an indication of the content of particulate material accumulated on said filter medium.

7. An apparatus for detecting the accumulation of particulate material collected on a filter medium formed of dielectric material in a chamber having the property of a microwave transmission line, said apparatus comprising:

means for exciting said chamber with an amplitude modulated RF excitation signal within a predetermined microwave frequency band; and means for monitoring the transmission loss of said signal through said chamber to sense the effective dielectric loss factor thereof to provide an indication of the content of particulate material accumulated on said filter medium.

8. An apparatus for detecting the accumulation of particulate material on a filter medium formed of dielectric material in a chamber having the property of a microwave transmission line, said apparatus comprising:

means for exciting said chamber with an amplitude modulated RF excitation signal in the microwave range of frequencies;

means for detecting the signal strength of said signal prior to exciting said chamber to produce a signal representative of the initial strength of said excitation signal;

means for detecting the signal strength of said signal subsequent to transmission thereof through said chamber to produce a signal representative of the final strength of said excitation signal; and means for comparing said initial strength signal and said final strength signal to produce a signal representative of the transmission loss of said signal through said chamber to detect changes in the effective dielectric loss factor thereof, said signal indicating the content of particulate material accumulated on said filter medium.

9. An apparatus as defined in claim 8, said means for exciting said chamber including means for varying the frequency of said excitation signal within a predetermined frequency band.

10. An apparatus as defined in claim 9, said means for varying the frequency of said signal being operable to vary the frequency within a frequency band of up to one octave.

* * * * *